(12) United States Patent
Zarembo et al.

(10) Patent No.: US 7,571,010 B2
(45) Date of Patent: Aug. 4, 2009

(54) CABLE ELECTRODE ASSEMBLY FOR A LEAD TERMINAL AND METHOD THEREFOR

(75) Inventors: Paul E. Zarembo, Vadnais Heights, MN (US); Mohan Krishnan, Shoreview, MN (US); Christopher P. Knapp, Ham Lake, MN (US); Russell L. Hoeker, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 421 days.

(21) Appl. No.: 11/123,321

(22) Filed: May 6, 2005

(65) Prior Publication Data
US 2006/0253180 A1  Nov. 9, 2006

(51) Int. Cl.
*A61N 1/18* (2006.01)
*A61N 1/05* (2006.01)
*A61B 5/0402* (2006.01)

(52) U.S. Cl. .................. 607/115; 607/148; 607/122; 600/372; 600/395

(58) Field of Classification Search ............ 607/2, 607/115, 131, 148, 116, 119, 122, 127; 600/372–375, 600/377, 395
See application file for complete search history.

(56) References Cited

U.S. PATENT DOCUMENTS

| | | | |
|---|---|---|---|
| 3,474,791 A | 10/1969 | Bentov | |
| 3,788,329 A * | 1/1974 | Friedman | 607/122 |
| 4,541,440 A * | 9/1985 | Parsonnet | 607/132 |
| 5,090,422 A | 2/1992 | Dahl et al. | |
| 5,483,022 A | 1/1996 | Mar | |
| 5,702,437 A | 12/1997 | Baudino et al. | |
| 5,760,341 A | 6/1998 | Laske et al. | |
| 5,796,044 A | 8/1998 | Cobian et al. | |
| 5,824,026 A | 10/1998 | Diaz | |
| 5,836,946 A | 11/1998 | Diaz et al. | |
| 5,845,396 A | 12/1998 | Altman et al. | |
| 5,928,277 A * | 7/1999 | Laske et al. | 607/122 |
| 6,137,060 A | 10/2000 | Avellanet | |
| 6,139,511 A | 10/2000 | Huter et al. | |
| 6,161,047 A | 12/2000 | King et al. | |
| 6,168,570 B1 | 1/2001 | Ferrera | |
| 6,191,365 B1 | 2/2001 | Avellanet | |
| 6,259,937 B1 | 7/2001 | Schulman et al. | |
| 6,259,954 B1 | 7/2001 | Conger et al. | |
| 6,292,702 B1 | 9/2001 | King et al. | |
| 6,295,476 B1 | 9/2001 | Schaenzer | |
| 6,399,886 B1 | 6/2002 | Avellanet | |
| 6,400,992 B1 | 6/2002 | Borgersen et al. | |
| 6,434,430 B2 | 8/2002 | Borgersen et al. | |
| 6,442,435 B2 | 8/2002 | King et al. | |
| 6,475,169 B2 | 11/2002 | Ferrera | |
| 6,477,427 B1 | 11/2002 | Stolz et al. | |
| 6,477,429 B1 | 11/2002 | Conger et al. | |
| 6,498,043 B1 | 12/2002 | Schulman et al. | |

(Continued)

*Primary Examiner*—Carl H Layno
*Assistant Examiner*—Natasha N Patel
(74) *Attorney, Agent, or Firm*—Schwegman, Lundberg & Woessner, P.A.

(57) ABSTRACT

A lead assembly includes a lead body and at least one cables at least partially disposed within the lead body. The cable has a non-electrode portion and an electrode portion, where the non-electrode portion extends within the lead body, and the electrode portion is external to the lead body.

19 Claims, 7 Drawing Sheets

U.S. PATENT DOCUMENTS

| | | |
|---|---|---|
| 6,671,544 B2 | 12/2003 | Baudino |
| 6,714,822 B2 | 3/2004 | King et al. |
| 6,720,497 B1 | 4/2004 | Barsne |
| 6,721,604 B1 | 4/2004 | Robinson et al. |
| 6,920,361 B2 * | 7/2005 | Williams .................... 607/122 |
| 7,031,777 B2 * | 4/2006 | Hine et al. .................. 607/122 |

* cited by examiner

CABLE ELECTRODE ASSEMBLY FOR A LEAD TERMINAL AND METHOD THEREFOR

TECHNICAL FIELD

Cable electrode assembly for leads that conduct electrical signals to and from tissue and an energy source.

TECHNICAL BACKGROUND

Pacemaker leads represent the electrical link between the pulse generator and tissue such as heart tissue, which is to be excited and/or sensed. These pacemaker leads include single or multiconductors that are connected to an electrode in an electrode assembly at an intermediate portion or distal end of a lead. A connector is included at the proximal end to form the electrical connection with the pacemaker.

When leads with multiple conductors are involved, the conductors are individually, mechanically and electrically coupled with the pulse generator at a proximal end of the multiple conductors. The multiple conductors at the proximal end are electrically insulated from each other to prevent shorts and limit electrical leakage between conductors. However, conventional assemblies are bulky and are relatively large for multi-polar assemblies. Furthermore, conventional assemblies have manufacturing drawbacks, for example, the assembly process is difficult and time consuming for electrodes, and the assembly process results in potentially less reliable interconnects.

Accordingly, what is needed is an improved electrode assembly that does not add to the overall diameter of the lead assembly.

SUMMARY

A lead assembly includes a lead body and at least one cable at least partially disposed within the lead body. The cable has a non-electrode portion and an electrode portion, such as a shocking electrode, where the non-electrode portion extends within the lead body, and the electrode portion is external to the lead body. Several options for the lead assembly include, but are not limited to, a termination member associated with a portion of the cable. Other options include forming multiple electrode portions along the lead, and/or using multiple cables to form the electrode portions.

A method includes disposing a cable along a leady body, where the cable has an electrode portion and a non-electrode portion. The non-electrode portion is disposed within an inner lumen of the lead body, such as a lumen of a coiled conductor. The method further includes disposing the electrode portion along an exterior portion of the lead body and forming at least one electrode, for example, by winding the cable around an outer surface of the lead body. The method further includes terminating the at least one cable within the inner lumen of the lead body.

These and other embodiments, aspects, advantages, and features will be set forth in part in the description which follows, and in part will become apparent to those skilled in the art by reference to the following description and referenced drawings or by practice thereof. The aspects, advantages, and features are realized and attained by means of the instrumentalities, procedures, and combinations particularly pointed out in the appended claims and their equivalents.

DESCRIPTION OF THE EMBODIMENTS

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope is defined by the appended claims.

Figure 1:
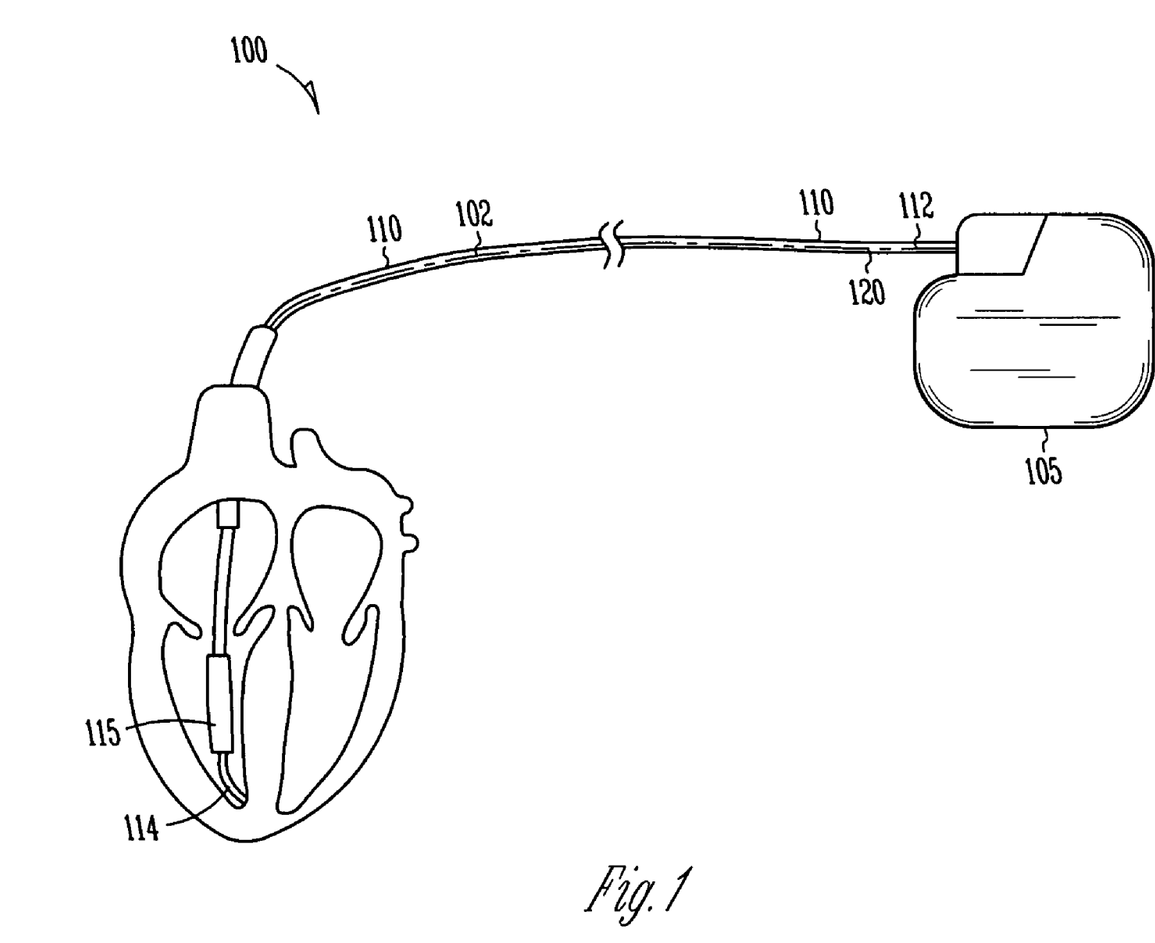
FIG. 1 is a diagram illustrating a lead system constructed in accordance with one embodiment.

An implantable device 100, such as a lead 102 for use with an electrical stimulator 105, is illustrated in FIG. 1. The implantable device 100 includes a lead 102 having a lead body 110, and at least one elongate conductor 120 contained within the lead body 110. The lead body 110 extends from a proximal portion 112 to a distal portion 114. The proximal portion 112 of the lead is electrically coupled with the electrical stimulator 105, for example, with a connector assembly.

In one option, the electrical stimulator 105 is a pulse sensor and generator that contains electronics to sense various electrical signals of the heart and also produce current pulses for delivery to the heart. The pulse sensor and generator also contains electronics and software necessary to detect certain types of arrhythmias and to correct for them.

The implantable device 100 further includes, in one option, one or more electrodes 115, for example, a shocking electrode. The one or more electrodes 115 are each electrically coupled with the at least one conductor 120. The electrode 115 allows for electrical signals to be delivered to the tissue from the electrical stimulator 105. The implantable device 100 further includes, in one option, features to allow the lead body 110 to be fixated within a patient. For example, in one option, the lead body 110 includes passive fixation features, such as one or more times. In another option, the lead body 110 includes an active fixation assembly, such as a fixation helix.

Figure 2:
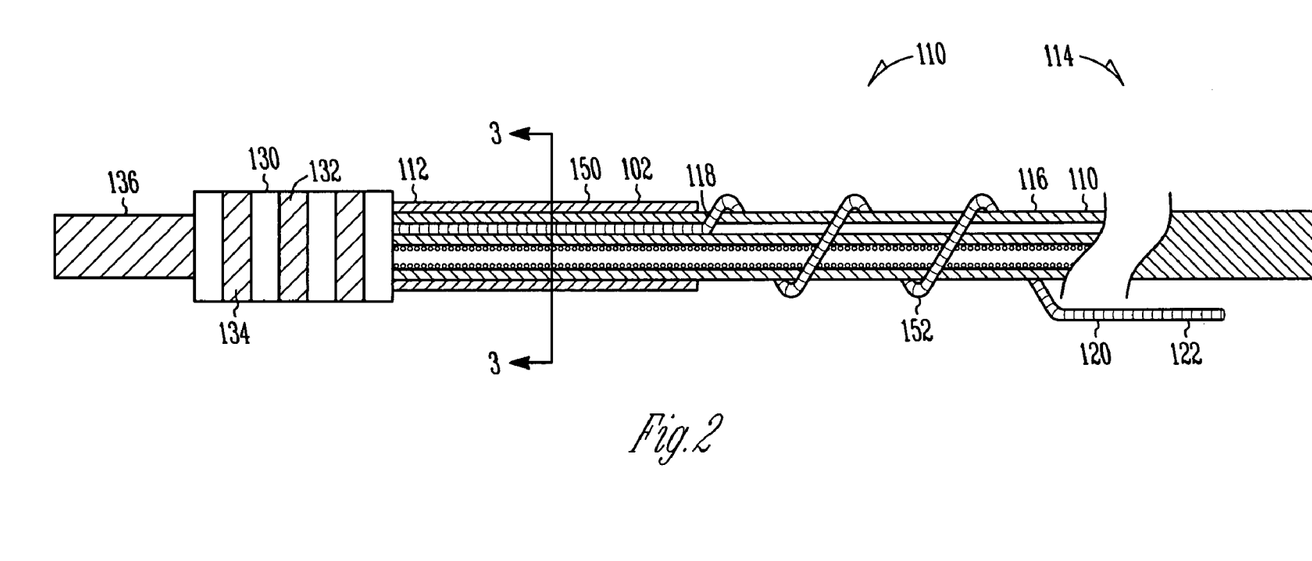
FIG. 2 is a partial cross-sectional view of a portion of a lead constructed in accordance with at least one embodiment.

Referring to FIG. 2, a terminal connector assembly 130 and conductor 120 of the lead assembly 110 are illustrated in greater detail, where one example of a multipolar inline lead terminal is illustrated. The terminal connector assembly 130 is configured to physically mate with a pulse sensor and generator, and to electrically couple with the pulse sensor and generator. In one example, the connector assembly 130 includes one or more electrodes 132, such as, for example, three terminal rings 134. The terminal connector assembly 130 further includes a terminal pin 136.

The conductor 120 is electrically and optionally mechanically coupled with the terminal connector assembly 130, for example, the terminal, near the proximal portion 112 of the lead 102. The conductor 120 includes, for example, at least one cable 122 or a coiled conductor 124. Cable strands can optionally be made of different materials or coatings to allow for biocompatibility, corrosion resistance, and optionally to achieve optimal capacitance. Examples of suitable materials for the cable strands include, but are not limited to, Pt clad Ta, Ti, Ta, Pt, Pt/Ir, Pt clad MP35N/Ag core, or combinations thereof. Other options for the cable include drugs that can be deposited between cable strand wires (e.g. to lower inflammation and decrease thresholds for pacing.) The at least one cable 122 includes, but is not limited to, a single cable, multiple cables, or twisted pair.

Figure 3:
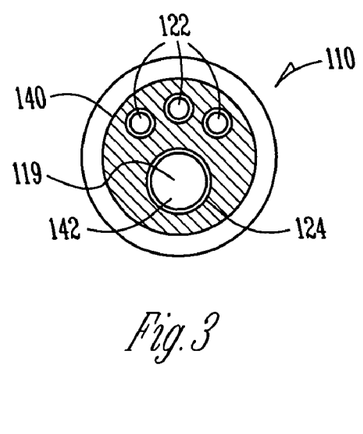
FIG. 3 is a cross-sectional view of a lead taken along 3-3 of FIG. 2.

The cable 122 extends from a proximal end of the lead 102 along the lead body 110 toward the distal end of the lead, although not necessarily extending to the distal end of the lead 102. The lead body 110 includes one or more lumens therein, as illustrated in FIG. 3, where FIG. 3 is a cross-section along FIG. 2. In one option, a plurality of cable lumens 140 are disposed within the lead body 110, and adjacent thereto is at least one first inner lumen 142. Optionally, the lumen 142 is greater in diameter than the cable lumens 140, for example, is sized to receive a coiled conductor 124 therein. The first inner lumen 142, in another option, is longitudinally spaced from the cable lumens 140, and in another option, is electrically insulated from the cable lumens 140.

Referring again to FIG. 2, the cable(s) 122 extends from the terminal connection near the proximal portion of the lead 102, and extends along the lead 102 within the cable lumen 140 along a non-electrode portion 150. At an intermediate portion of the lead 102, the cable 122 exits from the cable lumen 140 to an exterior surface 116 of the lead body 110, for example, through an exit lumen 118. The cable 122 is disposed along the exterior surface 116 of the lead body 110 to form the electrode portion 152, for example, the shocking electrode. In at least one option, the cable 122 is wrapped around the perimeter of the lead body 110, for example the exterior surface 116, to form the electrode. The cable 122 reenters the lead body 110, for example, and is terminated within a first inner lumen 142, such as lumen 140.

Figure 4:
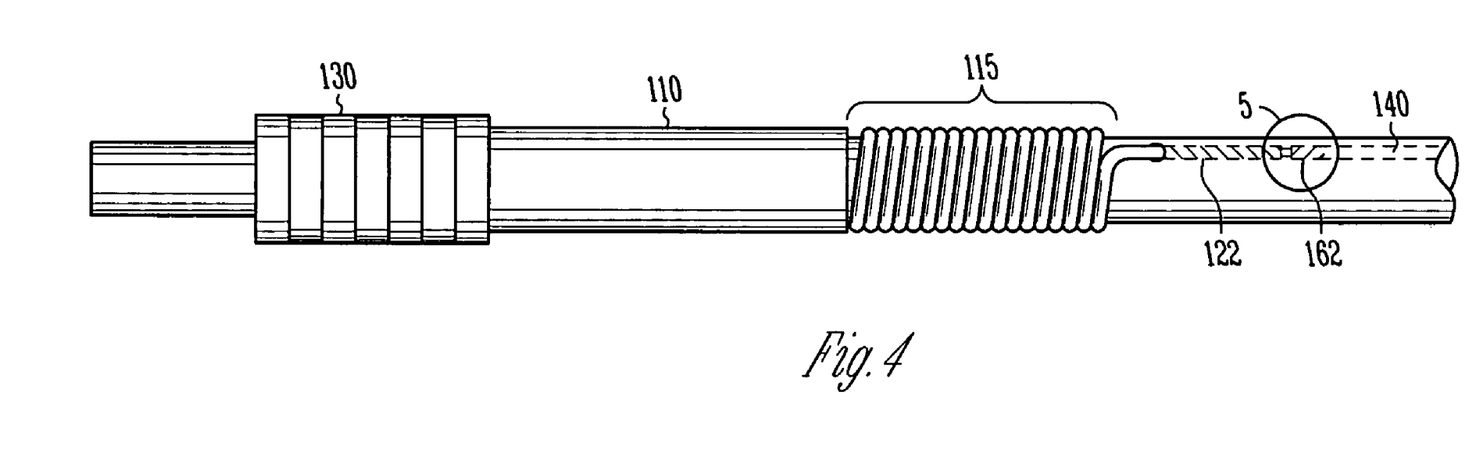
FIG. 4 is a side elevational view of a lead constructed in accordance with at least one embodiment.
Figure 5:
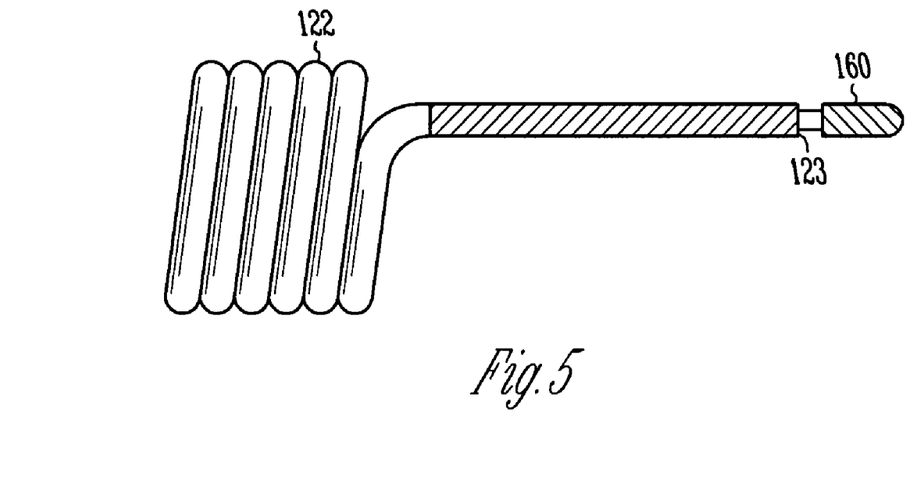
FIG. 5 is a side elevational view of a portion of a lead constructed in accordance with at least one embodiment.
Figure 6:
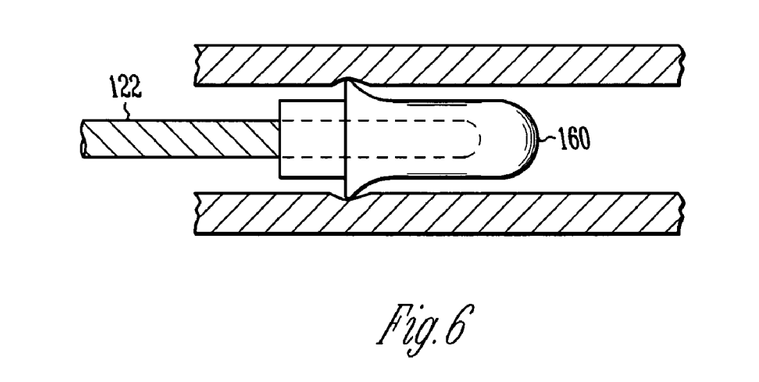
FIG. 6 is a cross-sectional view of a portion of a lead constructed in accordance with at least one embodiment.

FIGS. 4-6 illustrate additional options for the cable 122. The cable 122 is connected with the terminal connector assembly 130 as discussed above and extends along the lead within the lead body 110. The cable 122 exits the lead body 110 or is otherwise exposed to form an electrode 115, such as the shocking electrode. The cable 122 reenters the lead body 110 and is disposed within the cable lumen 140. The cable 122 is terminated within the cable lumen 140. In one option, as illustrated in FIG. 5, a terminating member 160 is disposed over a distal end 123 of the cable 122. The terminating member 160, or termination member, in one option, is non-conductive. In one option, polymer tubing is optionally disposed over the distal end 123 of the cable 122, and is optionally coupled with a fusion bond or an adhesive bond within the cable lumen 140 at 162. In another option, the terminating member 160 includes a tube coupled with the distal end 123, for example by swaging, crimping, welding, adhesive bonding as illustrated in FIG. 6. Further options for terminating the distal end include, but are not limited to, a metal tube, non conductive polymer tube, passive electrical component, an inductive coil, a capacitor, adhesives, and fused components, such as heat shrink tubing.

Figure 7:
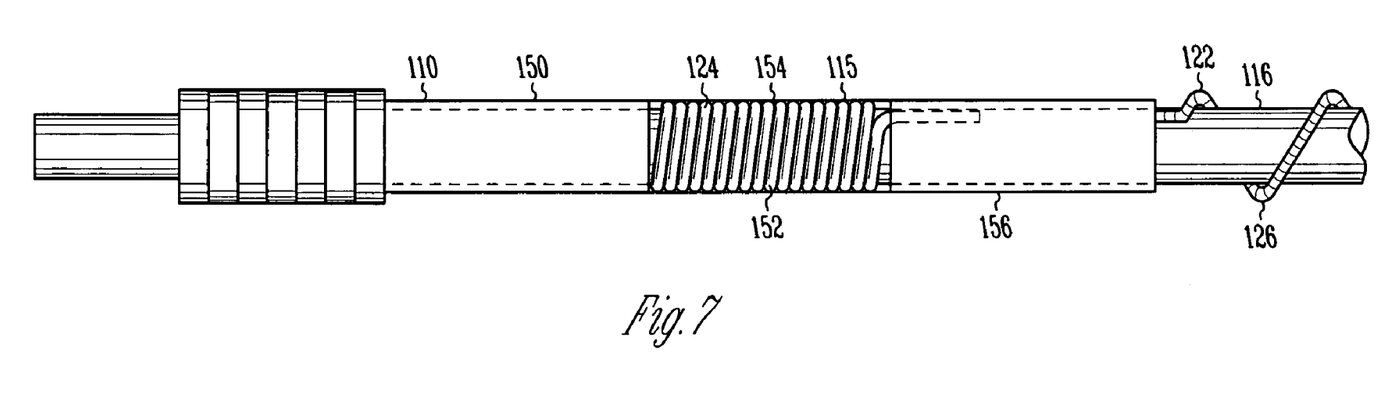
FIG. 7 is a side elevational view of a lead constructed in accordance with at least one embodiment.

Alternatively, the distal end 123 of the cable 122 or terminating member 160 could be secured within the cable lumen 140 by adhesive, fusion bonding, or decreasing the size of the lumen with heat or laser. Another example to secure the distal end 123 or terminating member 160 would include a mechanical feature that allows for insertion, but assists in preventing or prevents extraction. FIG. 7 illustrates another embodiment for the lead assembly that can be incorporated with any of the above or below discussed options. It should be noted that an example termination member mechanically and non-redundantly terminates the cable distal end 123.

The cable 122 is disposed about the external portion 116 of the lead body 110 to form the electrode 115, for example, as discussed above. The lead assembly further includes an electrically porous member 154 disposed over the electrode portion 152. In one option, the electrically porous member 154 is a tube disposed over the electrode 115, and in another option, secures the cable 122 in place. The electrically porous member 154, in one example, in slid over or coated on the cable 124 prior to winding the cable 124 into its shape. In a further option, the member 154 is sintered on to the cable.

In another option, a second member 156 such as an outer layer of polymer tube or polymer wrap is bonded over at least a portion of the cable 122 to assist in making the lead isodiametric, and/or secures the cable 122 in place. The electrically porous member 154 is optionally secured to the lead body 110 and/or the electrode 115. In an option, the electrically porous member 154 is secured in place with adhesive, a fusion bond, shrink tubing, or other types of mechanically coupling mechanisms.

The electrically porous member 154 assists in preventing ingrowth of scar tissue, and further allows for extraction of the lead. Examples of suitable materials include, but are not limited to, expanded PTFE (ePTFE) or ultra high molecular weight polyethyleve (UHMWPE), or other biocompatible electrically porous materials. The electrically porous member 154 further assists in optimizing electrical properties.

In another embodiment, multiple cables 122 are used with the lead assembly in various configurations. One example is illustrated in FIG. 7. A first cable 124 is disposed along a first longitudinal location, and a second cable 126 is disposed along a second longitudinal location, where the at least two cables are insulated from one another. For example, insulative material is disposed between the two longitudinally spaced cables either as separate lumen or insulation on cable(s). In another example, the first cable 124 is disposed along a first lumen for the non-electrode portion 150 and the second cable 126 is disposed along a second lumen for the non-electrode portion 150. It should be noted that there can be additional cables and/or electrodes present, as well.

Figure 8:
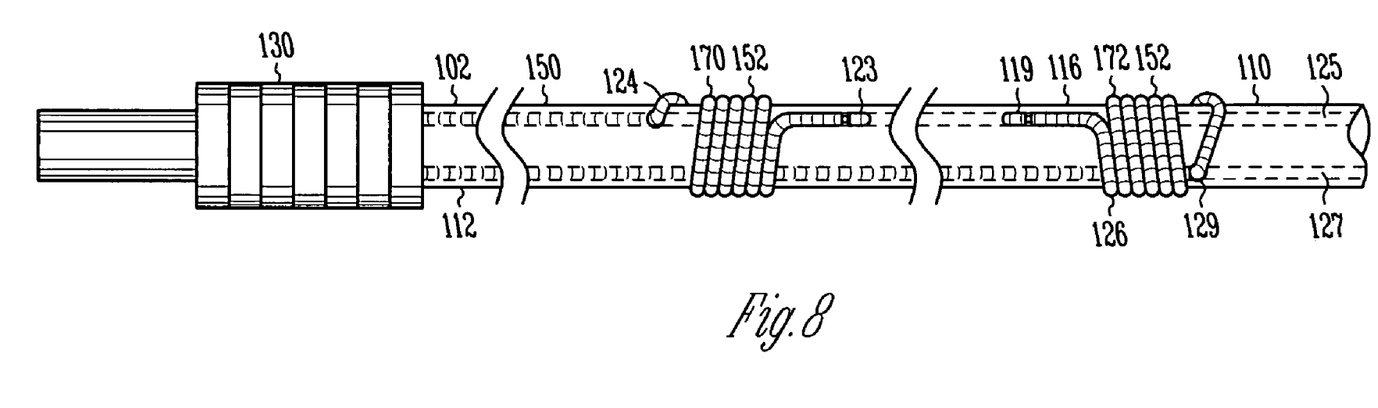
FIG. 8 is a side elevational view of a lead constructed in accordance with at least one embodiment.

FIG. 8 illustrates the first and second cables 124, 126 having electrode portions 152 at two separate longitudinal portions 170, 172, which is also illustrated in FIG. 7. Again referring to FIG. 8, in one option, the first cable 124 extends from the terminal connector assembly 130 along a first cable lumen 125 to form a non-electrode portion 150 and exiting to form the electrode portion 152 at a first longitudinal location 170, and returning to a first cable lumen 125. In one option, the first cable 124 is wrapped around the lead body 110, for example, toward the distal end of the lead to form the electrode portion 152. The first cable 124 terminates at a first cable distal end 123, for example, along an intermediate portion of the lead 102. The first cable distal end 123 is disposed distal to the electrode portion 152 at the first longitudinal location 170. The direction of the current wave of the electrode portion 152 at location 170 (the proximal electrode) is toward distal end 123, and toward the distal end of the lead.

A second cable 126 is electrically coupled with the terminal connector assembly 130 and extends along a second cable lumen 127 to form a non-electrode portion 150. The second cable extends 126 longitudinally past the first cable electrode portion 152 and exits the second cable lumen 127 at 129 to form the electrode portion 152 at a second longitudinal location 172, for example, by wrapping the cable around an exterior portion 116 of the lead body 110. In one option, the second cable 126 is wrapped toward the proximal portion 112 of the lead body 110 to form the electrode portion 152. The second cable 126 re-enters the lead body 110 and is terminated in one option at 119 within the first cable lumen 125, and is spaced from the first cable distal end 123. In another option, the second cable 126 can be disposed within another empty lumen of the lead body 110. It should be noted that there can be additional cables and/or electrodes present, as well.

The second cable 126 distal end is disposed more proximal to the proximal end of the lead than the electrode portion at location 172 (the distal electrode). The direction of the current wave, in one option, of the electrode portion 152 at location 172 is toward the proximal end of the lead. The current wave directions in opposite direction can be used to optimize defibrillation threshold and cadioversion.

Figure 9:
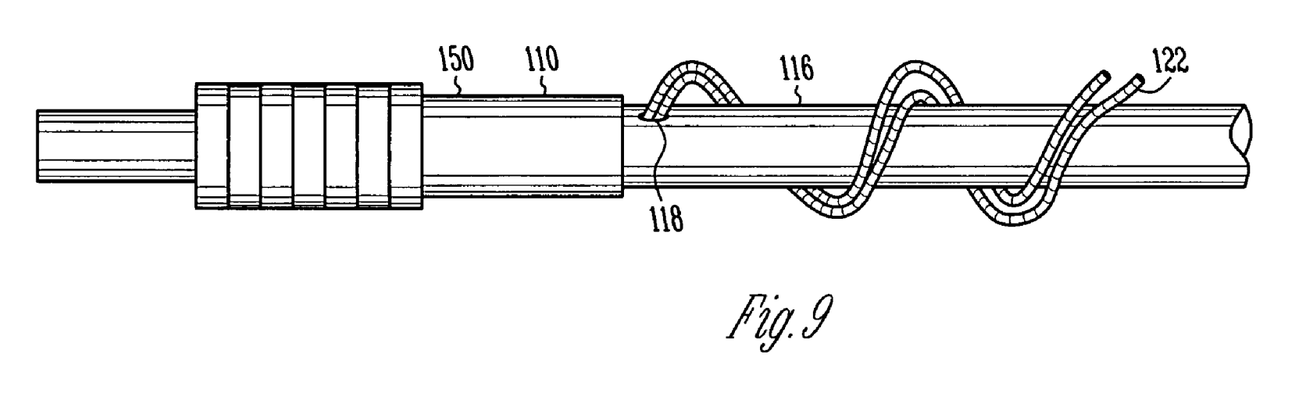
FIG. 9 is a side elevational view of a portion of a lead constructed in accordance with at least one embodiment.
Figure 10:
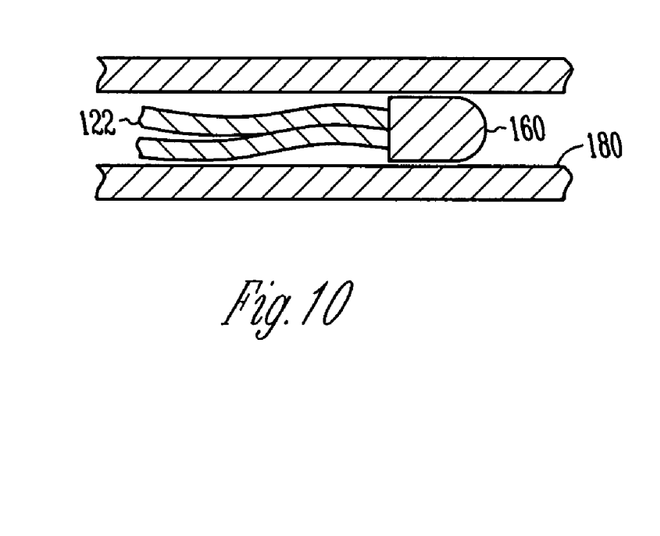
FIG. 10 is a cross-section view of a portion of a lead constructed in accordance with at least one embodiment.

FIGS. 9-12 illustrate additional embodiments for multi-cable leads, for example, to lower the conductor resistance going to the electrode. In one option, the cables 122, for example multiple cables, are wound about an exterior portion 116 of the lead body 110 to form an electrode portion 152. The cables 122, in one option, exit from at least one lumen, for example from a single exit lumen 118, as shown in FIG. 9. The cables 122 extend in a substantially parallel relationship along the lead body 110, and re enter the lead body 110 into at least one lumen, for example, a single lumen 180, as shown in FIG. 10. Optionally, a terminating member 160 is coupled with a distal end 123 of the cables 122. The terminating member 160 can be coupled by swaging or crimping a tube on the end 123 of the cable 122. The terminating member 160 can be secured within the lumen 180, for example, by a press fit, interference fit, adhesive, or otherwise.

Figure 11:
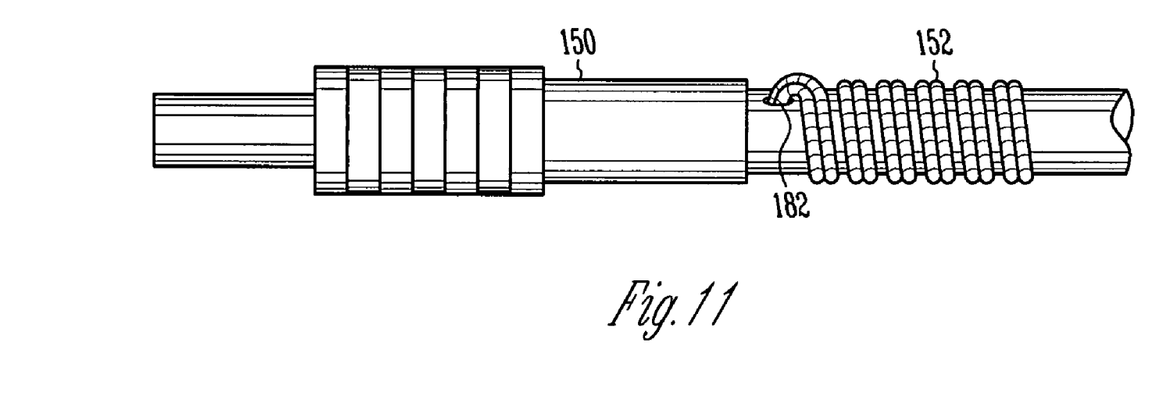
FIG. 11 is a side elevational view of a portion of a lead constructed in accordance with at least one embodiment.
Figure 12:
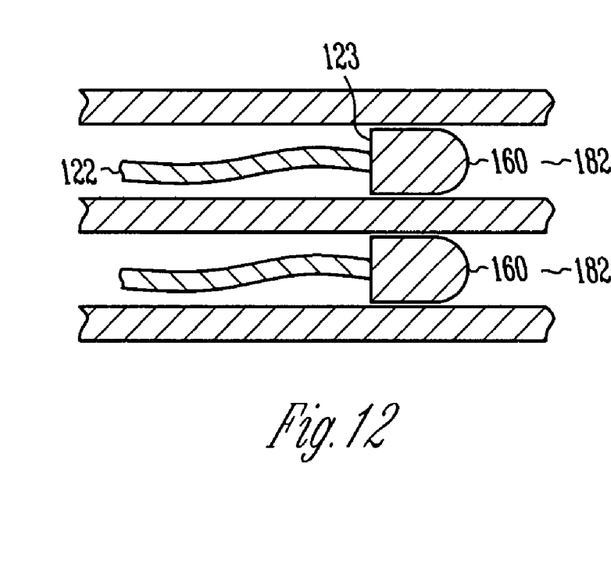
FIG. 12 is a cross-section view of a portion of a lead constructed in accordance with at least one embodiment.

The cables 122, in another option, exit from multiple lumens 182, for example as shown in FIG. 11. The cables 122 extend in a substantially parallel relationship along the lead body 110, and re-enter the lead body 110 into multiple lumens 182, as shown in FIG. 12. Optionally, a terminating member 160 is coupled with a distal end 123 of each of the cables 122.

Figure 13:
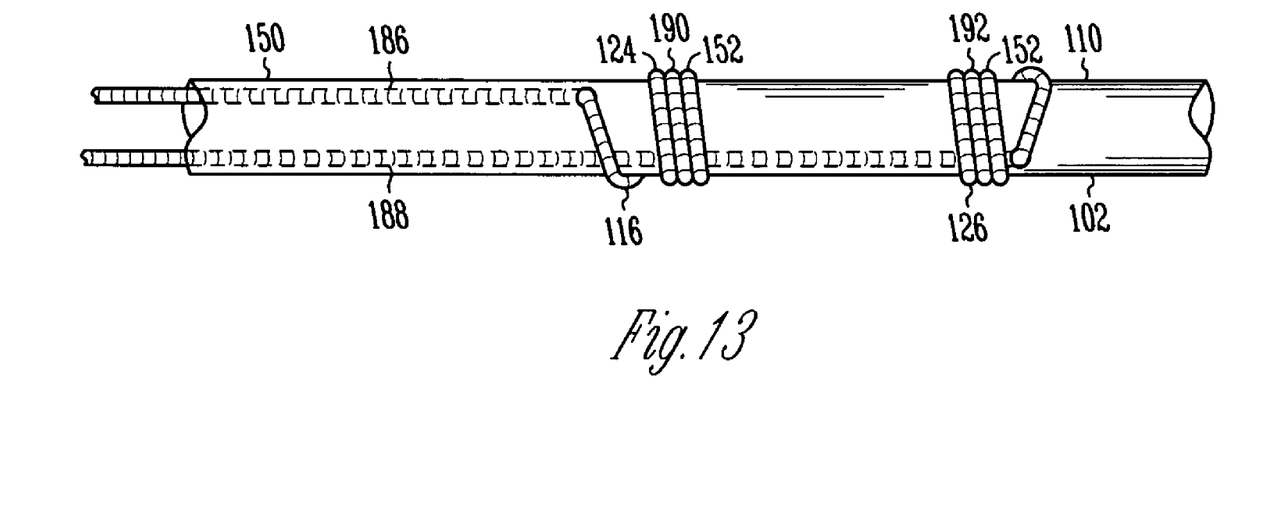
FIG. 13 is a side elevational view of a portion of a lead constructed in accordance with at least one embodiment.
Figure 14:
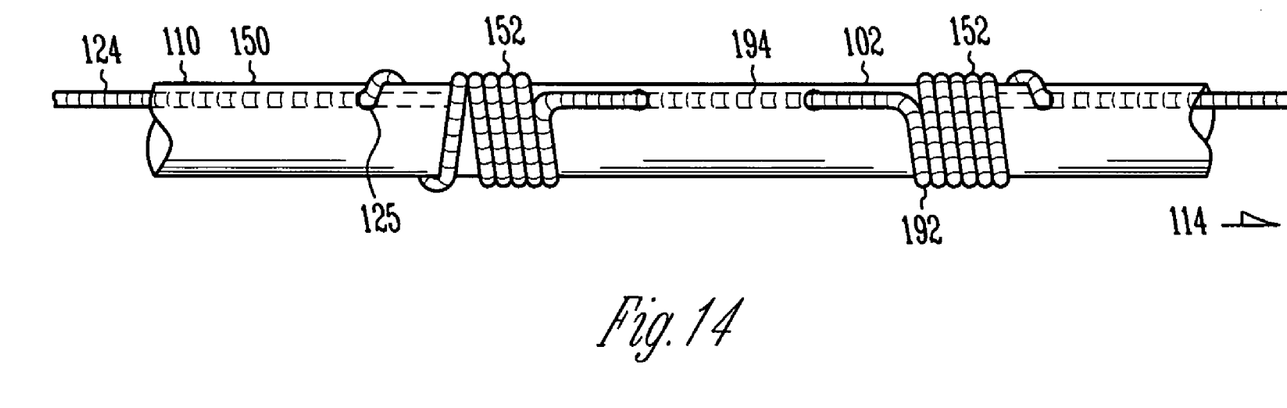
FIG. 14 is a side elevational view of a portion of a lead constructed in accordance with at least one embodiment.

FIGS. 13 and 14 illustrate additional examples for the lead assembly having multiple electrode portions 152, for example electrodes connected to the same conductor to form an electrode array. FIG. 13 illustrates a first cable 124 that is routed from the terminal connector assembly along and within the lead body 110 to form the non-electrode portion 150. The first cable 124 extends along a first lumen 186 and exits the first lumen to form the electrode portion 152, and optionally at least a first electrode portion 190 and a second electrode portion 192, where the first electrode portion 190 is longitudinally spaced from the second electrode portion 192. It should be noted that more than two electrode portions can be formed from the first cable 124.

In one option, the first cable 124 is wound about an outer portion 116 of the lead body 110 to form the electrode portion. In another option, the first cable 124 exits the first lumen 186, and the first cable 124 is wound back over the non-electrode portion 150 toward a proximal end 112 of the lead 102 and re-enters the second cable lumen 188. The first cable 124 is electrically connected with the terminal connector assembly. This allows for a redundant connection to the electrode shocking coils, and therapy can be delivered despite disruptions to the cable.

FIG. 14 illustrates another example for the lead assembly. A first cable 124 is routed, for example, from the terminal connector assembly along and within the lead body 110 to form a non-electrode portion 150, and exiting from a first cable lumen 125 to form an electrode, for example a shocking electrode. The first cable 124, in one option, is wrapped around a portion of the lead body 110, and re-enters the lead body 110 within the first cable lumen 125 to extend along a second non-electrode 194 portion. It should be noted that other lumens can be used as well. The first cable 124 exits the first cable lumen 125 from the second non-electrode portion 194 to form a second electrode portion 192 that is longitudinally spaced from the other electrode portion 190. In one option, the second electrode portion 192 includes the first cable 124 that is wrapped around the lead body 110. The cable re-enters the lead body 110 and extends toward the distal end portion 114 of the lead 102. This could be repeated for the cable 122 as the single cable could be made into multiple coil electrodes. For example, expanded tachy therapies, multiple common electrodes may be necessary. This allows for the ability to add multiple common electrodes without adding joints or connections, and simplies creating the electrode for future therapies such as CRFD, AF, etc.

During use of the device, the lead having the electrode formed of the cable(s), including the various options discussed above, is introduced within the vasculature of a patient. The energy source, such as the pulse generator and sensor, is implanted subcutaneously within the patient. The connector assembly is electrically coupled with the energy source. For example, the connector assembly is inserted into a socket of the energy source, and the in-line connector assembly, including the connector electrodes form an electrical connection within the energy source.

A method for forming the device, including the devices discussed above, includes disposing at least one cable through a lumen of a lead body, and threading or otherwise having the cable exit the lead body through an exit lumen. The cable is wound about the lead body, for example, toward a distal end portion of the lead to form an electrode, such as a shocking electrode. The cable is threaded back into the lead body and is terminated within, for example, the cable lumen or a lumen of a coiled conductor. In another option, a terminating member such as a polymer or metal tube is secured to a distal end portion of the cable. Multiple electrodes, for example, at two or more longitudinal locations of the lead, are optionally formed with one or more cables, where the cables can be insulated between the two or more electrodes. The multiple electrodes can be wound in directions opposite to one another.

Another cable can be optionally introduced with the first cable, for example in parallel, to create a redundant relationship, where each or two or more cable are electrically coupled with a terminal assembly of the lead. Alternatively, the second cable can have a non-parallel disposition relative to the first cable, as discussed above. Each of the cables may be electrically coupled with each other, or can be insulated from one another. For each of the above methods, the electrode portion, in an option, is for pacing and sensing, where the electrode is used for pacing and sensing electrical signals.

Advantageously, the lead assembly allows for the elimination of supplemental joints between the cables/conductors and the electrodes, resulting in improved reliability due to less connections. Furthermore, since the supplemental connection can be eliminated, the lead diameter can be made smaller, while allowing more surface area of the electrode to be presented in electrical contact with tissue. This can lower the system surface impedance, which increases energy deliverable to the patient.

It is to be understood that the above description is intended to be illustrative, and not restrictive. Although the use of the implantable device has been described for use as a lead in, for example, a cardiac stimulation system, the implantable device could as well be applied to other types of body stimulating systems, such as neurological systems and leads. Many other embodiments will be apparent to those of skill in the art upon reviewing the above description. The scope should, therefore, be determined with reference to the appended claims, along with the full scope of equivalents to which such claims are entitled.

What is claimed is:

1. A lead assembly comprising:
   a lead body extending from a proximal end portion to a distal end portion, the lead body having at least one inner lumen and one or more exit lumens;
   at least one cable disposed within at least a portion of the lead body, the at least one cable having at least two coiled electrode portions and non-electrode portions;
   the non-electrode portions of the cable extending along within the inner lumen of the lead body, the at least two coiled electrode portions exiting through at least one of the exit lumen and coiled around an exterior portion of the lead body and forming electrodes; and
   at least one non-electrode portion disposed between a first coiled electrode portion and a second coiled electrode portion, the first coiled electrode portion coiled in an opposite direction as the second coiled electrode portion.

2. The lead assembly as recited in claim 1, further comprising means for terminating a distal end of at least one cable.

3. The lead assembly as recited in claim 1, wherein the at least two coiled electrode portions are disposed at separate longitudinal portions.

4. The lead assembly as recited in claim 1, wherein at least one of the two coiled electrode portions includes a cable coiling around the lead body toward the proximal end portion of the lead body.

5. The lead assembly as recited in claim 1, wherein the first coiled electrode portion coils toward a distal end portion, and the second coiled electrode portion coils toward the proximal end portion.

6. A lead assembly comprising:
   a lead body extending from a proximal end portion to a distal end portion, the lead body having at least one inner lumen and one or more exit lumens;
   at least two cables disposed parallel to one another within at least a portion of the lead body, the at least two cables each having at least one electrode portion and at least one non-electrode portion; and
   the non-electrode portions of the cable extending along within the at least one inner lumen of the lead body, the at least two cables exiting through at least one of the exit lumens and are coiled around an exterior portion of the lead body and forming a first coiled electrode portion and a second coiled electrode portion, and a current wave of the first coiled electrode portion is toward the distal end portion and a current wave of the second coiled electrode portion is toward the proximal end portion.

7. The lead assembly as recited in claim 6, wherein the at least one cable extends continuously from a first end to a second end, and the first and second ends are electrically coupled to a terminal connector assembly.

8. The lead assembly as recited in claim 6, wherein the at least two cables are disposed in separate lumens.

9. The lead assembly as recited in claim 6, wherein the at least one electrode portion includes two electrodes, and the two electrodes are longitudinally spaced from one another.

10. The lead assembly as recited in claim 6, wherein a first cable is wrapped around the lead body toward the distal end portion.

11. The lead assembly as recited in claim 6, wherein a first cable has a cable proximal end and a cable distal end, and the cable distal end is disposed distal to the electrode.

12. The lead assembly as recited in claim 6, wherein the at least two cables include a first cable and a second cable, the first and second cables terminate in a first lumen.

13. The lead assembly as recited in claim 12, wherein distal ends of the first and second cables are spaced from one another.

14. The lead assembly as recited in claim 6, wherein the first coiled electrode portion coils toward a distal end portion, and the second coiled electrode portion coils toward the proximal end portion.

15. The lead assembly as recited in claim 6, wherein at least one of the two coiled electrode portions includes a cable coiling around the lead body toward the proximal end portion of the lead body.

16. A method comprising:
    disposing at least one cable along a lead body, the lead body extending from a proximal end portion to a distal end portion, the at least one cable having at least one electrode portion and at least one non-electrode portion;
    disposing the at least one non-electrode portion of the cable within an inner lumen of the lead body;
    disposing the at least one electrode portion along an exterior portion of the lead body and forming at least one electrode, and coiling a first electrode portion in an opposite direction as a second electrode portion; and
    terminating the at least one cable within the inner lumen of the lead body.

17. The method as recited in claim 16, further comprising winding two or more electrodes around the exterior portion of the lead.

18. The method as recited in claim 17, wherein winding two or more electrodes includes winding the two or more electrodes from a single cable.

19. The method as recited in claim 16, further comprising stripping insulation from an insulated cable to form the at least one electrode.

* * * * *

UNITED STATES PATENT AND TRADEMARK OFFICE
CERTIFICATE OF CORRECTION

PATENT NO. : 7,571,010 B2 Page 1 of 1
APPLICATION NO. : 11/123321
DATED : August 4, 2009
INVENTOR(S) : Zarembo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 728 days.

Signed and Sealed this

Seventh Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,571,010 B2
APPLICATION NO. : 11/123321
DATED : August 4, 2009
INVENTOR(S) : Zarembo et al.

It is certified that error appears in the above-identified patent and that said Letters Patent is hereby corrected as shown below:

Title page, in field (57), under "Abstract", in column 2, line 1, delete "cables" and insert -- cable --, therefor.

In column 8, line 64, below "Claim 19" insert
--20. The lead assembly as recited in claim 1, wherein the cable extends continuously from a first end to a second end, and the first and second ends are electrically coupled to a terminal connector assembly.
21. The lead assembly as recited in claim 1, further comprising a termination member mechanically coupled with a cable distal end portion, the termination member mechanically coupled within the inner lumen.
22. The lead assembly as recited in claim 1, further comprising an electrically porous member disposed over at least one electrode.
23. The lead assembly as recited in claim 22, wherein the electrically porous member is not bonded with the lead body.
24. The lead assembly as recited in claim 6, further comprising at least one termination member mechanically coupled with a cable distal end portion, the termination member mechanically coupled within the inner lumen.
25. The lead assembly as recited in claim 24, wherein termination members are mechanically coupled with each cable distal end portion, and a first cable distal end portion is disposed within a first inner lumen and a second cable distal end portion is disposed within a second inner lumen.
26. The lead assembly as recited in claim 6, further comprising an electrically porous member disposed cover at least one electrode.
27. The method as recited in claim 16, further comprising mechanically coupling a terminating member a distal portion of the cable, and mechanically coupling the terminating member within the inner lumen of the lead body.
28. The method as recited in claim 16, further comprising retaining the electrode portion in position along the lead body with an electrically porous member.--.

Signed and Sealed this
Tenth Day of April, 2012

David J. Kappos
*Director of the United States Patent and Trademark Office*

UNITED STATES PATENT AND TRADEMARK OFFICE
CERTIFICATE OF CORRECTION

PATENT NO.       : 7,571,010 B2
APPLICATION NO.  : 11/123321
DATED            : August 4, 2009
INVENTOR(S)      : Zarembo et al.

It is certified that error appears in the above-identified patent and that said Letters Patent is hereby corrected as shown below:

Delete the title page and substitute therefor the attached title page showing the corrected number of claims in patent.

Title page, in field (57), under "Abstract", in column 2, line 1, delete "cables" and insert -- cable --, therefor.

In column 8, line 64, below "Claim 19" insert
--20. The lead assembly as recited in claim 1, wherein the cable extends continuously from a first end to a second end, and the first and second ends are electrically coupled to a terminal connector assembly.
21. The lead assembly as recited in claim 1, further comprising a termination member mechanically coupled with a cable distal end portion, the termination member mechanically coupled within the inner lumen.
22. The lead assembly as recited in claim 1, further comprising an electrically porous member disposed over at least one electrode.
23. The lead assembly as recited in claim 22, wherein the electrically porous member is not bonded with the lead body.
24. The lead assembly as recited in claim 6, further comprising at least one termination member mechanically coupled with a cable distal end portion, the termination member mechanically coupled within the inner lumen.
25. The lead assembly as recited in claim 24, wherein termination members are mechanically coupled with each cable distal end portion, and a first cable distal end portion is disposed within a first inner lumen and a second cable distal end portion is disposed within a second inner lumen.
26. The lead assembly as recited in claim 6, further comprising an electrically porous member disposed cover at least one electrode.

This certificate supersedes the Certificate of Correction issued April 10, 2012.

Signed and Sealed this
First Day of May, 2012

David J. Kappos
*Director of the United States Patent and Trademark Office*

27. The method as recited in claim 16, further comprising mechanically coupling a terminating member a distal portion of the cable, and mechanically coupling the terminating member within the inner lumen of the lead body.

28. The method as recited in claim 16, further comprising retaining the electrode portion in position along the lead body with an electrically porous member.--.

(12) United States Patent
Zarembo et al.

(10) Patent No.: US 7,571,010 B2
(45) Date of Patent: Aug. 4, 2009

(54) CABLE ELECTRODE ASSEMBLY FOR A LEAD TERMINAL AND METHOD THEREFOR

(75) Inventors: Paul E. Zarembo, Vadnais Heights, MN (US); Mohan Krishnan, Shoreview, MN (US); Christopher P. Knapp, Ham Lake, MN (US); Russell L. Hoeker, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 421 days.

(21) Appl. No.: 11/123,321

(22) Filed: May 6, 2005

(65) Prior Publication Data
US 2006/0253180 A1 Nov. 9, 2006

(51) Int. Cl.
*A61N 1/18* (2006.01)
*A61N 1/05* (2006.01)
*A61B 5/0402* (2006.01)

(52) U.S. Cl. .......... 607/115; 607/148; 607/122; 600/372; 600/395

(58) Field of Classification Search .......... 607/2, 607/115, 131, 148, 116, 119, 122, 127; 600/372, 375, 600/377, 395
See application file for complete search history.

(56) References Cited

U.S. PATENT DOCUMENTS

| | | | |
|---|---|---|---|
| 3,474,791 A | 10/1969 | Bentov | |
| 3,788,329 A * | 1/1974 | Friedman | 607/122 |
| 4,541,440 A * | 9/1985 | Parsonnet | 607/132 |
| 5,090,422 A | 2/1992 | Dahl et al. | |
| 5,483,022 A | 1/1996 | Mar | |
| 5,702,437 A | 12/1997 | Baudino et al. | |
| 5,760,341 A | 6/1998 | Laske et al. | |
| 5,796,044 A | 8/1998 | Cobian et al. | |
| 5,824,026 A | 10/1998 | Diaz | |
| 5,836,946 A | 11/1998 | Diaz et al | |
| 5,845,396 A | 12/1998 | Altman et al. | |
| 5,928,277 A * | 7/1999 | Laske et al. | 607/122 |
| 6,137,060 A | 10/2000 | Avellanet | |
| 6,139,511 A | 10/2000 | Huter et al. | |
| 6,161,047 A | 12/2000 | King et al. | |
| 6,168,570 B1 | 1/2001 | Ferrera | |
| 6,191,365 B1 | 2/2001 | Avellanet | |
| 6,259,937 B1 | 7/2001 | Schulman et al. | |
| 6,259,954 B1 | 7/2001 | Conger et al. | |
| 6,292,702 B1 | 9/2001 | King et al. | |
| 6,295,476 B1 | 9/2001 | Schaenzer | |
| 6,399,886 B1 | 6/2002 | Avellanet | |
| 6,400,992 B1 | 6/2002 | Borgersen et al. | |
| 6,434,430 B2 | 8/2002 | Borgersen et al. | |
| 6,442,435 B2 | 8/2002 | King et al | |
| 6,475,169 B2 | 11/2002 | Ferrera | |
| 6,477,427 B1 | 11/2002 | Stolz et al. | |
| 6,477,429 B1 | 11/2002 | Conger et al. | |
| 6,498,043 B1 | 12/2002 | Schulman et al. | |

(Continued)

*Primary Examiner*—Carl H Layno
*Assistant Examiner*—Natasha N Patel
(74) *Attorney, Agent, or Firm*—Schwegman, Lundberg & Woessner, P.A.

(57) ABSTRACT

A lead assembly includes a lead body and at least one cable at least partially disposed within the lead body. The cable has a non-electrode portion and an electrode portion, where the non-electrode portion extends within the lead body, and the electrode portion is external to the lead body.

28 Claims, 7 Drawing Sheets